United States Patent [19]

Sims et al.

[11] Patent Number: 4,849,687

[45] Date of Patent: Jul. 18, 1989

[54] STEAM QUALITY MONITORING MEANS AND METHOD

[75] Inventors: Jackie C. Sims; Donald J. Dowling; Richard S. Simpson, all of Houston, Tex.

[73] Assignee: Texaco Inc., White Plains, N.Y.

[21] Appl. No.: 125,507

[22] Filed: Nov. 25, 1987

[51] Int. Cl.⁴ .............................................. G01R 27/26
[52] U.S. Cl. .................................. 324/61 R; 73/61 R
[58] Field of Search ........... 324/61 R, 61 QS, 61 QL, 324/61 P; 73/61 R, 61.1 R, 29

[56] References Cited

U.S. PATENT DOCUMENTS

| | | | |
|---|---|---|---|
| 3,437,924 | 4/1969 | Tocanne | 324/61 R |
| 4,119,950 | 10/1978 | Redding | 73/24 |
| 4,658,208 | 4/1987 | Lee et al. | 324/61 R |
| 4,769,593 | 9/1988 | Reed et al. | 324/61 R |

Primary Examiner—Reinhard J. Eisenzopf
Assistant Examiner—Maura K. Regan
Attorney, Agent, or Firm—Robert A. Kulason; James J. O'Loughlin; Ronald G. Gillespie

[57] ABSTRACT

A steam quality monitor monitoring the quality of steam flowing in the pipe includes capacitance sensing apparatus which senses the capacitance of the flowing steam and provides a capacitance signal corresponding to the said capacitance. Another sensor which may be either a temperature sensor or a pressure sensor senses either the temperature or pressure of the steam and provides a representative type signal. Circuitry connected to the capacitance sensor and to the temperature or pressure sensor provides an output corresponding to the quality of steam in accordance with the capacitance and the temperature or pressure signal.

12 Claims, 1 Drawing Sheet

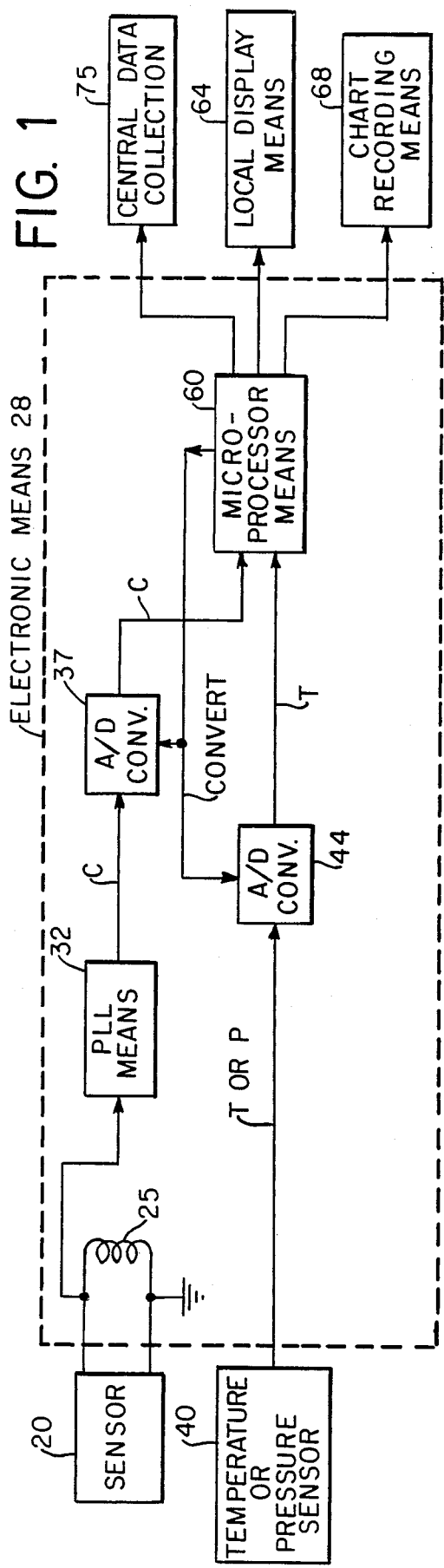
FIG. 1
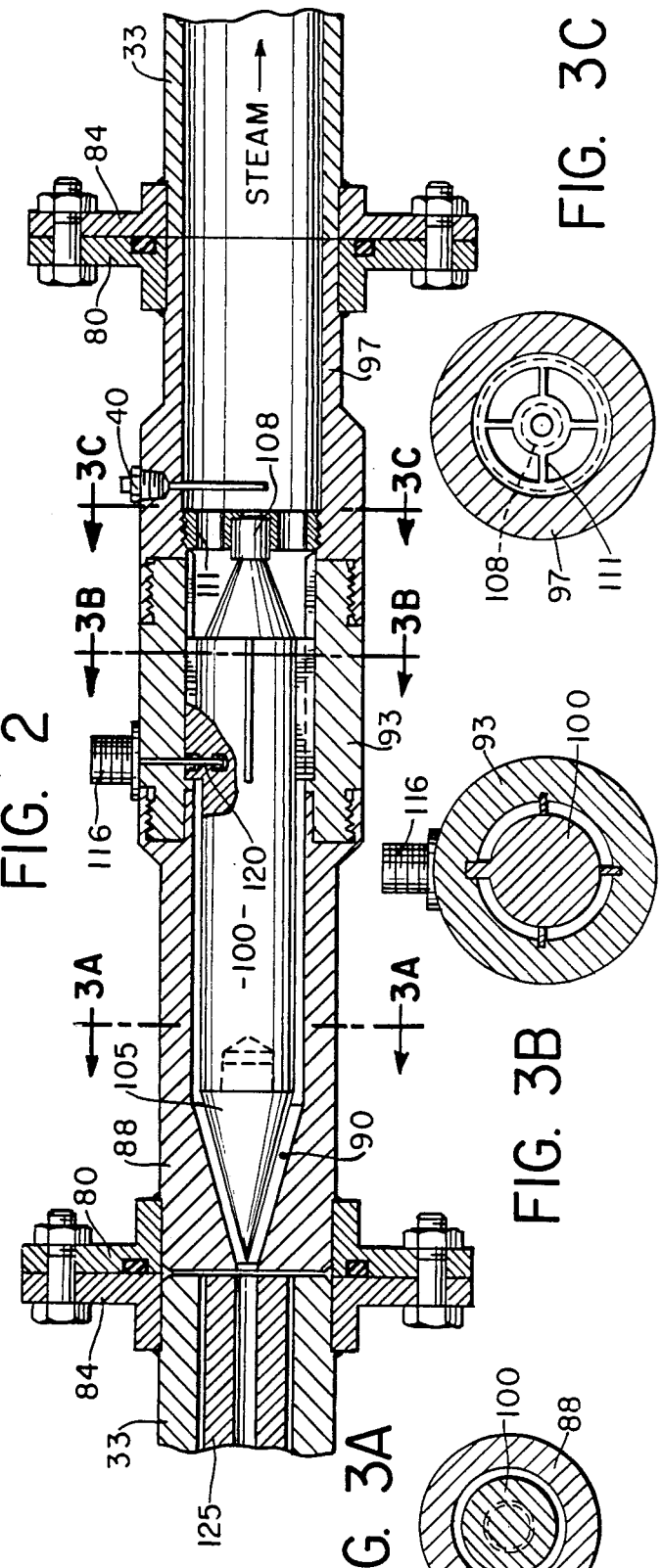
FIG. 2
FIG. 3A
FIG. 3B
FIG. 3C

STEAM QUALITY MONITORING MEANS AND METHOD

BACKGROUND OF THE INVENTION

Field of the Invention

The present invention relates to monitoring means and method in general and more specifically to steam quality monitoring means and method.

SUMMARY OF THE INVENTION

A steam quality monitor monitoring the quality of steam flowing in the pipe includes capacitance sensing apparatus which senses the capacitance of the flowing steam and provides a capacitance signal corresponding to the said capacitance. Another sensor which may be either a temperature sensor or a pressure sensor senses either the temperature or pressure of the steam and provides a representative type signal. Circuitry connected to the capacitance sensor and to the temperature or pressure sensor provides an output corresponding to the quality of steam in accordance with the capacitance and the temperature or pressure signal.

The objects and advantages of the invention will appear more fully hereinafter, from a consideration of the detailed description which follows, taken together with the accompanying drawings wherein one embodiment is illustrated by way of example. It should be expressly understood, however, that the drawings are for illustrative purposes only and are not to be construed as defining the limits of the invention.

DESCRIPTION OF THE DRAWINGS

FIG. 1 is a simplified block diagram of a steam quality monitor constructed in accordance with the present invention.

FIG. 2 is an assembly type drawing of the steam sensor shown in FIG. 1.

FIGS. 3A, 3B and 3C are cross-sectional drawings of the steam sensor shown in FIG. 2.

DESCRIPTION OF THE INVENTION

Enhanced Oil Recovery (EOR) operations on petroleum reservoirs are increasing the use of reservoir steam flooding to improve the hydrocarbon sweep efficiency.

It has been found that steam qualities of 80% and below, often provide better treatment of the field than "dry" or superheated steam. In addition, lower quality steam floods reduced the fuel cost in a given field by a significant amount.

To maximize the benefits of steam floods, it is important that the quality of steam being supplied to each injector well be known as accurately as possible.

Steam quality at the generator can be calculated from consumed fuel, feedwater, and generator factors, information which is available in the field. As the steam passes down long pipelines, divides at manifolds, and passes through inclined and right angle pipe connections, the steam quality at any given point becomes uncertain. This is due primarily to the fact that "wet" steam (steam of less than 100% quality) is made up of two fluid phases flowing in the lines. These phases are the steam vapor - often called the gas phase, and the hot water - referred to as the liquid phase.

Typically, these phases have significantly different physical characteristics (density, viscosity, etc.) and flow at different velocities in the pipelines. Accordingly, as the manifolds and pipe connections force changes in flow direction and as the elevation of the pipelines themselves magnify the gravitational effects on the phases, the steam quality at any given point in the line becomes less predictable. Consequently, the steam quality actually entering a given well in a multi-well field is not normally known very accurately. In order to establish the quality at the well head, field personnel will often open the steam flow line and connect a trailer-mounted apparatus into the steam line feeding the well. The two phases on the trailer are separated using settling tanks and demisters, and their quantities are measured. The phases are then returned to the line downstream.

The respective vapor and liquid measurements are combined to calculate steam quality.

While this method is accurate, it is time consuming to produce the final determination and requires the services of skilled personnel.

In addition, a trailer-mounted device is quite expensive and alone could not provide a "snapshot" of all the wells in the entire field.

Reservoir engineers, who must adjust steam quality at the well head to optimize the field steam sweep, and those who computer model the field steam flood, could use an unmanned steam quality indicator, constructed in accordance with the present invention, at every well head. This information could be read at the well head and/or sent by electronic means to the field office and other locations for immediate field-wide correlation.

With reference to FIG. 1, a capacitive type sensor 20 is connected across a coil 25 which is part of the electronics 28. Sensor 20 provides a signal to phase lock loop means 32 which in turn provides a signal C related to the capacitance of the steam flowing through a pipe 33. Signal C is provided to an analog-to-digital converter 37. A temperature or pressure sensor 40 located in pipe 33 provides a signal T or P corresponding to the sensed temperature or the sensed pressure of the steam in pipe 33. The sensed parameter is used in conjunction with steam tables which have been stored in microprocessor means, as hereinafter explained. There are conventionally two steam tables, one related to temperature and the other related to pressure. Either steam table may be used.

Analog-to-digital converters 37, 44 convert analog signals C and T or P, respectively to digital signals C and T, respectively, in response to a 'convert' signal provided by microprocessor means 60. Microprocessor means 60 derives the steam quality as hereinafter explained and provides signals relating to the steam quality to local display means 64, to chart recorder means 68 and to central data collection 75. Local display means 67 displays the steam quality right at the monitoring site while chart recorder means 68 makes a record of the steam quality. Further, central data collection 75 permits a plurality of steam quality monitors as hereinbefore described to monitor steam flowing to a plurality of wells without the need to go to each specific monitoring site.

Microprocessors means 60 utilizes the T or P digital signals along with stored conventional steam tables information to derive the corrected densities $P_V$ and $P_W$ of vapor and water respectively. Microprocessor means 60 employs $P_V$ and $P_W$ in determining the steam quality X from the following equation 1.

$$X = (C^n - C_v^n K_w^n) / [(1 - P_w/P_v)C^n - C_v^n K_w^n + (P_w/P_v)C_v^n K_v^n]$$

1.

where C is sensed capacitance, $C_V$ is the capacitance of vapor, $K_V$ is in the dielectric constant of vapor, $K_W$ is the dielectric constant of the water at the sensed temperature, and n is an exponent related to the geometry of the steam water particles.

Equation 1 was derived as follows:
The definition of steam quality X is $$X = M_V/(M_V + M_W) \qquad 2.$$

where $M_V$=mass of the vapor and $M_W$=mass of the water
Equation 2 may be rewritten as:

$$X = 1/[1 + M_w/M_v] \qquad 3.$$

Replacing mass by the product of density times volume $$X = 1/[1 + (P_w/P_v)(V_w/V_v)] \qquad 4.$$

where $V_V$ is the volume of the vapor, $V_W$ is the volume of the water, $P_V$ is the corrected density of the vapor, and $P_W$ is a corrected density of the water (corrected for steam line pressure and temperature). The vapor volume fraction, $\lambda$, of the total volume of wet steam is:

$$\lambda = V_V/(V_V + V_W) \qquad 5.$$

Solving for $V_W/V_V$ yields $$V_W/V_V = (1 - \lambda)/\lambda \qquad 6.$$

Using equation 6 to replace $V_W/V_V$ in equation 4 yields $$X = \lambda/[(1 - P_W/P_V)\lambda + P_W/P_V] \qquad 7.$$

The vapor volume fraction, $\lambda$, can be related to the dielectric constant of the wet steam by the standard Lichtenecker Rother equation $$K^n = \lambda K_v^n + (1 - \lambda) K_w^n \qquad 8.$$

where K=dielectric constant of the wet steam
Solving equation 8 for $\lambda$ yields $$\lambda = (K^n - K_w^n)/(K_v^n - K_w^n) \qquad 9.$$

Substituting this value of $\lambda$ in equation 7

$$X = (K^n - K_w^n)/[(1 - P_W/P_V)K^n - K_w^n + (P_W/P_V)K_v^n] \qquad 10.$$

When wet steam passes between the electrodes of capacitance sensor 20, the measured capacitance is related to the dielectric constant of the steam by the following equation:

$$C = gK \qquad 11.$$

Where g=constant for specific sensor (g takes into account the geometry of the sensor)
When the sensor is filled with 100% vapor which has a dielectric constant of one, when g will equal the sensed capacitance, $C_V$, of the vapor. Thus equation 11 may be written as:

$$C = C_V K \quad \text{or} \qquad 12.$$

$$K = C/C_V \qquad 13.$$

By using the value of K from equation 13 in equation 10 it yields equation 1.

Referring now to FIGS. 2 and 3, sensor 20 is connected in line with pipe 33. Sensor 20 includes threaded flanges 80 which are bolted to flanges 84 threaded onto pipes 33. An element 88, having an internal passageway 90 for steam to flow through, forms part of a capacitor and is threaded into a flange 80. An insulator 93 is connected to element 88 and to another element 97. Element 97 is threaded into another flange 80 thus forming the inline connection. The other 'plate' of the capacitor is element 100 which has an insulator deflector 105. Element 100 is supported downstream by an insulator 108 and a bracket 111.

An electrical connector 116 is attached to element 88 and insulator 93. It is important that there is an electrical connection between element 88 and electrical connector 116. An electrical connection element 120 of connector 116 is connected to element 100 so that elements 88 and 100 form the capacitor.

Although not part of steam sensor 20, a flow control choke 125 is located in pipe 33. Any other device for constricting the steam may be used. For convenience temperature sensor 40 is mounted on element 97 but it is not part of steam sensor 20.

The steam in pipe 33 flows through steam sensor 20 and hence between capacitive elements 88 and 100 and forms the dielectric. Capacitive elements are electrically connected through connector 116 and connection element 120 to coil 25.

What is claimed is:
1. A monitor which monitors the quality of steam flowing in a pipe comprising:
capacitance sensing means for sensing the capacitance of the flowing steam and providing a capacitance signal corresponding thereto,
temperature sensing means for sensing the temperature of the flowing steam and providing a temperature signal representative of the sensed temperature, and
output means, connected to the capacitance sensing means and to the temperature sensing means, for providing an output corresponding to the quality of the steam in accordance with the capacitance signal and the temperature signal; and
in which the capacitance sensing means includes:
a first capacitive element having a small opening at one end and a larger opening at another end,
first insulator means connected to the first capacitor element having a through opening larger than the largest opening of the first capacitor element,
a second capacitive element mounted inside of the first capacitive element having an outer diameter at one point less than the diameter of the largest opening of the first capacitive element so as to form a cylindrical channel for the flow of steam,
deflection means attached to the second capacitive element for deflecting the steam entering the small opening of the first capacitive element into the channel formed by the first and second capacitive elements,
connector means for providing electrical connections to the two capacitive elements, and
structural means connected to the insulator means for forming a body in cooperation with the insulator means and the first capacitive element suitable for incline connection with the pipe carrying the steam.

2. A monitor as described in claim 1 in which the output means includes:
an analog-to-digital converter connected to the capacitance sensing means for converting the capacitance signal to digital capacitance signals,
a second analog-to-digital converter means connected to the temperature sensing means for converting the temperature signal to digital temperature signals, and
microprocessor means connected to both analog-to-digital converter means for providing the output.

3. A monitor as described in claim 2 in which the sensing means further includes:
a coil connected across the capacitive elements and with one of its ends connected to ground, and
phase lock loop means connected to an ungrounded end of the coil for providing the capacitance signal in accordance with the capacitance of the steam flowing between the capacitive elements.

4. A monitor which monitors the quality of steam flowing in a pipe comprises:
capacitance sensing means for sensing the capacitance of the flowing steam and providing a capacitance signal corresponding thereto,
pressure sensing means for sensing the pressure of the flowing stream and providing a pressure signal representative of the sensed pressure,
output means connected to the capacitance sensing means and to the pressure sensing means for providing an output corresponding to the quality of the steam in accordance with the capacitance and the temperature signals; and
in which the capacitance sensing means includes:
a first capacitive element having a small opening at one end and a larger opening at another end,
first insulator means connected to the first capacitor element having a through opening larger than the largest opening of the first capacitor element,
a second capacitive element mounted inside of the first capacitive element having an outer diameter at one point less than the diameter of the largest opening of the first capacitive element so as to form a cylindrical channel for the flow of steam,
deflection means attached to the second capacitive element for deflecting the steam entering the small opening of the first capacitive element into the channel formed by the first and second capacitive elements,
connector means for providing electrical connections to the two capacitive elements, and
structural means connected to the insulator means for forming a body in cooperation with the insulator means and the first capacitive element suitable for inline connection with the pipe carrying the steam.

5. A monitor as described in claim 4 in which the output means includes:
an analog-to-digital converter connected to the sensing means for converting the capacitance signal to digital capacitance signals,
a second analog-to-digital converter means connected to the pressure sensing means for converting the pressure signal to digital pressure signals, and
microprocessor means connected to both analog-to-digital converter means for providing the output.

6. A monitor as described in claim 5 in which the sensing means includes:
a coil connected across the capacitive elements and with one of its ends connected to ground, and
phase lock loop means connected to another end of the coil for providing the capacitance signal in accordance with the capacitance of the steam flowing between the capacitive elements.

7. A method for monitoring the quality of steam comprising the steps of:
sensing the capacitance of the steam,
providing a capacitance signal corresponding to the sensed capacitance of the steam,
sensing the temperature of the steam,
providing a temperature signal representative of the sensed temperature of the steam,
providing an output corresponding to the quality of the steam in accordance with the capacitance signal and the temperature signal; and
in which the step includes:
using a first capacitive element having a small opening at one end and a larger opening at another end,
connecting a first insulator to the first capacitor element having a through opening larger than the largest opening of the first capacitor element,
mounting a second capacitive element mounted inside the first capacitive element having an outer diameter at one point less than the diameter of the largest opening of the first capacitive element so as to form a cylindrical channel for the flow of steam,
deflecting the steam entering the small opening of the first capacitive element with a deflector into the channel formed by the first and second capacitive elements,
providing electrical connections to the two capacitive elements, and
forming a structural body in cooperation with the insulator and the first capacitive element suitable for in line connection with a pipe carrying the steam.

8. A method as described in claim 7 in which the output step includes:
converting the capacitance signal to digital capacitance signals,
converting the temperature signal to digital temperature signals, and
providing the output in accordance with the capacitance digital signals and the temperature digital signals.

9. A method as described in claim 8 in which the sensing step includes:
connecting a coil across the capacitive elements,
connecting one end of the coil to ground, and
connecting phase lock loop means to another end of the coil for providing the capacitance signal in accordance with the capacitance of the steam flowing between the capacitive elements.

10. A method for monitoring the quality of steam comprising the steps of:
sensing the capacitance of the steam,
providing a capacitance signal corresponding to the sensed capacitance of the steam,
sensing the pressure of the steam, and
providing an output corresponding to the quality of the steam in accordance with the capacitance signal and the pressure signal; and
in which the sensing step includes:

using a first capacitive element having a small opening at one end and a larger opening at another end, connecting a first insulator means to the first capacitor element having a through opening larger than the largest opening of the first capacitor element, mounting a second capacitive element inside of the first capacitive element having an outer diameter at one point less than the diameter of the largest opening of the first capacitive element so as to form a cylindrical channel for the flow of steam, deflecting the steam entering the small opening of the first capacitive element with a deflector into the channel formed by the first and second capacitive elements, providing electrical connections to the two capacitive elements, and forming a structural body in cooperation with the insulator means and the first capacitive element for inline connection with a pipe carrying the steam.

11. A method as described in claim 10 in which the output step includes:

converting the capacitance signal to digital capacitance signals, converting the pressure signal to digital temperature signals, and providing the output in accordance with the capacitance digital signals and the pressure digital signals.

12. A method as described in claim 11 in which the sensing step includes:

connecting a coil connected across the capacitive elements, connecting one end of the coil to ground, connecting phase lock loop means to another end of the coil for providing the capacitance signal in accordance with the capacitance of the steam flowing between the capacitive elements.

* * * * *